United States Patent [19]

Long, Jr. et al.

[11] Patent Number: 5,264,220
[45] Date of Patent: Nov. 23, 1993

[54] METHOD OF EXTENDING THE VASCULAR DWELL-TIME OF PARTICULATE THERAPEUTIC AND PARTICULATE DIAGNOSTIC AGENTS

[76] Inventors: David M. Long, Jr., 10988 Horizon Hills Dr., El Cajon, Calif. 92020; Raymond A. Long, 301 Nautilus St., La Jolla, Calif. 92037

[21] Appl. No.: 790,855

[22] Filed: Nov. 12, 1991

[51] Int. Cl.$^5$ .............................................. A61K 9/121
[52] U.S. Cl. ...................................... 424/450; 514/46; 514/47; 514/814; 514/832
[58] Field of Search ................. 424/450; 514/814, 832, 514/46, 47

[56] References Cited

U.S. PATENT DOCUMENTS

| | | | |
|---|---|---|---|
| 4,397,846 | 4/1983 | Weiner | 514/772 |
| 4,675,310 | 6/1987 | Chapman | 514/75 |
| 4,758,431 | 7/1988 | Osterholm | 514/561 |
| 4,781,871 | 11/1988 | West et al. | 264/43 |
| 4,865,836 | 9/1989 | Long, Jr. | 424/5 |
| 4,873,346 | 10/1989 | Anderson | 548/157 |
| 4,927,623 | 5/1990 | Long, Jr. | 424/5 |
| 4,951,673 | 8/1990 | Long | 128/653 A |
| 4,987,154 | 1/1991 | Long, Jr. | 514/772 |
| 4,993,415 | 2/1991 | Long | 128/653 A |
| 5,051,353 | 9/1991 | Stratton | 435/2 |
| 5,055,479 | 10/1991 | Takiguchi et al. | 514/359 |
| 5,120,731 | 6/1992 | Meinert | 514/316 |

FOREIGN PATENT DOCUMENTS

WO91/14444 10/1991 PCT Int'l Appl. .

OTHER PUBLICATIONS

Chaplin, D. J. et al. "Effect of Nicotinamide on the Microregional Heterogeneity of Oxygen Delivery within a Murine Tumor" *Journal of the National Cancer Institute* 82(8): 672-676 (1990).

Chaplin, D. J. et al. "Nicotinamide, Fluosol DA and Carbogen: a Strategy to Reoxygenate Acutely and Chronically Hypoxic Cells *In Vivo*," *Br. J. Cancer* 63:109-113 (1991).

Núñez, R. et al. "Nicotinamide Coenzymes in Heart and Coronary Blood during Myocardial Infarction," *American Journal of Pathology* 226(1): 73-76 (1974).

Núñez, R. et al. "NAD Glycohydrolase Activity in Hearts with Acute Experimental Infarction," *American Journal of Pathology* 231(4): 1173-1177 (1976).

Shioi, Y. et al. "Selective Inhibition of Chlorophyll Biosynthesis by Nicotinamide," *Archives of Biochemistry and Biophysics* 267(1): 69-74 (1988).

Geyer, R. P. "Perfluorochemicals as Oxygen Transport Vehicles," *Biomat., Art. Cells, Art. Org.* 15(2): 329-332 (1987).

Moss, G. S. et al. "Polyhemoglobin and Fluorocarbon as Blood Substitutes," *Biomat., Art. Cells, Art. Org.* 15(2): 333-336 (1987).

Harasaki, H. et al. "Morphological Effects of Pyridoxalated-hemoglobin-polyoxyethylene Conjugate in Dogs," *Biomat., Art. Cells, Art. Org.* 15(2): 361 (1987).

Mattrey, R. F. and Long, D. C. "Potential Role of PFOB in Diagnostic Imaging," *Investigative Radiology* 23(S1): S298-S301 (1988).

(List continued on next page.)

*Primary Examiner*—Thurman K. Page
*Assistant Examiner*—G. S. Kishore
*Attorney, Agent, or Firm*—Pennie & Edmonds

[57] ABSTRACT

The present invention relates to a composition for increasing the vascular dwell-time of a particulate therapeutic or diagnostic agent in a mammal through the adjunct administration of an effective amount of the particulate therapeutic or diagnostic agent and an effective amount of a vascular dwell-time enhancing agent. Suitable therapeutic and diagnostic agents include those whose efficacy within the body is predicated on their ability to remain within or to be carried within the vascular compartment. Accordingly this method can be readily adapted for treating several diseases and disorders, including hypoxia, hypoxemia, anemia and cancer and for imaging selected regions of a mammal by various imaging techniques, including ultrasound imaging, X-ray imaging and MRI imaging.

33 Claims, No Drawings

OTHER PUBLICATIONS

Riess, J. G. "Blood Substitutes: Where Do We Stand with the Fluorocarbon Approach?," *Current Surgery* 45(5): 365-370 (1988).

Mattrey, R. F. "Potential Role of Perfluorooctylbromide in the Detection and Characterization of Liver Lesions with CT," *Radiology* 170: 18-20 (1989).

Spence, R. K. "Fluosol DA-20 in the Treatment of Severe Anemia: Randomized, Controlled Study of 46 Patients," *Critical Care Medicine* 18(11): 1227-1230 (1990).

Investigators Brochure on Fluosol DA-20%.

Pak, C. C. and Fidler, I. J. "Liposomal Delivery of Biological Response Modifiers to Macrophages," *Biotherapy* 3: 55-64 (1991).

Carlson, L. A. and Orö, L. "The Effects of Nicotinic Acid on the Plasma Free Fatty Acids," *Acta Medica Scandinavica* 172: 641-645 (1962).

Carlson, L. A. et al. "Effect of a Single Dose of Nicotinic Acid on Plasma Lipids in Patients with Hyperlipoproteinemia," *Acta Medica Scandinavica* 183: 457-465 (1968).

Skidmore, I. F. et al. "Effects of Nicotinic Acid and Some of its Homologues on Lipolysis, Adenyl Cylase, Phosphodiesterase and Cyclic AMP Accumulation in Isolated Fat Cells" *Pharmacology* 6: 330-338 (1971).

Luria, M. H. "Effect of Low-dose Niacin on High-density Lipoprotein Cholesterol and Total Cholesterol/High-density Lipoprotein Cholesterol Ratio," *Arch. Intern Med* 148: 2493-2495 (1988).

Datta, S. et al. "Enhanced Myocardial Preservation by Nicotinic Acid, an Antilipolytic Compound: mechanism of Action," *Basic Res Cardiol* 84: 63-76 (1989).

Superko, H. R. "Drug Therapy and the Prevention of Atherosclerosis in Humans," *Am. J. Cardiol.* 64: 31G-38G (1989).

Sauvage, J. P. et al. "Double-blind, Placebo-controlled, Multi-centre Trial of the Efficacy and Tolerance of Niflumic Acid ('Nifluril') Capsules in the Treatment of Tonsillitis in Adults," *Current Medical Research and Opinion* 11(10): 631-637 (1990).

*Physicians' Desk Reference*, 45th Ed. (Medical Economics Data 1991).

Beutler, B. et al. "Purification of Cachectin, a Lipoprotein Lipase-suppressing Hormone Secreted by Endotoxin-induced RAW 264.7 Cells," *J. Exp. Med.* 161: 984-995 (1985).

Torti, F. M. et al. "A Macrophage Factor Inhibits Adipocyte Gene Expression: An *In Vitro* Model of Cachexia," *Science* 229: 867-869 (1985).

Dinarello, C. A. et al. "Tumor Necrosis Factor (Cachectin) is an Endogenous Pyrogen and Induces Production of Interleukin 1," *J. Exp. Med.* 163: 1433-1450 (1986).

Price, S. R. et al. "Regulation of Lipoprotein Lipase Synthesis by Recombinant Tumor Necrosis Factor-the Primary Regulatory Role of the Hormone in 3T3-L1 Adipocytes" *Archives of Biochemistry and Biophysics* 251(2): 738-746 (1986).

Beutler, B. and Cerami, A. "Cachectin: More than a Tumor Necrosis Factor," *The New England Journal of Medicine* 316(7): 379-385 (1987).

Oliff, A. et al. "Tumors Secreting Human TNF/Cachectin Induce Cachexia in Mice," *Cell* 50: 555-563 (1987).

Tracey, K. J. et al. "Cachectin/Tumor Necrosis Factor Induces Cachexia, Anemia, and Inflammation," *J. Exp. Med.* 167: 1211-1227 (1988).

Agarwal, S. A. et al. "Tumor Necrosis Factor-mediated Cytotoxicity Involves ADP-ribosylation," *The Journal of Immunology* 140(12):4187-4192 (1988).

Pomposelli, J. J. et al. "Role of Biochemical Mediators in Clinical Nutrition and Surgical Metabolism," *Journal of Parenteral and Enteral Nutrition* 12(2):212-218 (1988).

Lähdevirta, J. et al. "Elevated Levels of Circulating Cachectin/Tumor Necrosis Factor in Patients with Acquired Immunodeficiency Syndrome," *The American Journal of Medicine* 85:289-291 (1988).

Maury, C. P. and Teppo, A-M. "Tumor Necrosis Factor in the Serum of Patients with Systemic Lupus Erythematosus," *Arthritis and Rheumatism* 32(2):146-150 (1989).

Beutler, B. and Cerami, A. "The Biology of Cachectin/TNF-a Primary Mediator of the Host Response," *Ann. Rev. Immunol.* 7:625-655(1989).

Perez, C. et al. "A Nonsecretable Cell Surface Mutant of Tumor Necrosis Factor (TNF) Kills by Cell-to-Cell Contact," *Cell* 63:251-258 (1990).

Schraufstätter, I. U. et al. "Cellular Targets of $H_2O_2$ and HOCl Induced Injury," *Basic Life Sci.* 49:833-837 (1988).

OTHER PUBLICATIONS

Pekala, P. H. and Moss, J. "Poly ADP-ribosylation of Protein," *Current Topics In Cellular Regulation* 22:1-49 (1983).

Sims, J. L. et al. "Poly (ADP-ribose) Polymerase Inhibitors Preserve Nicotinamide Adenine Dinucleotide and Adenosine 5'-Triphosphate Pools in DNA-damaged Cells: Mechanism of Stimulation of Unscheduled DNA Synthesis," *Biochemistry* 22:5188-5194 (1983).

Berger, N. A. et al. "Poly (ADP-ribose) Polymerase Mediates the Suicide Response to Massive DNA Damage: Studies in Normal and DNA-repair Defective Cells," *Japan Sci. Soc. Press*, pp. 219-226 (Miwa, M. et al. eds. 1983).

Schraufstätter, I. U. et al. "Hydrogen Peroxide-induced Injury of Cells and its Prevention by Inhibitors of Poly (ADP-ribose) Polymerase," *Proc. Natl. Acad. Sci., U.S.A.* 83:4908-4912 (1986).

Nadeau, D. and Lane, D. A. "The Cytotoxicity of Chrysotile Asbestos Fibers to Pulmonary Alveolar Macrophages. I. Effects of Inhibitors of ADP-ribosyl Transferase," *Cell Biology and Toxicology* 4(1):13-30 (1988).

Simpson, L. L. et al. "Production by *Clostridium spiroforme* of an Iotalike Toxin that Possesses Mono(ADP-ribosyl)transferase Activity: Identification of a Novel Class of ADP-ribosyltransferases," *Infection and Immunity* 57(1):255-261 (1989).

Pozzilli, P. et al. "Nicotinamide Increases C-peptide Secretion in Patients with Recent Onset Type I Diabetes," *Diabetic Medicine* 6:568-572 (1989).

August, E. M. et al. "Inhibition of Poly(Adenoisine Diphosphate-ribose) Polymerase by Thymidine and Thymidine Analogues in L1210 Cells and Its Relationship to the Potentiation of the Antitumor Activity of 1,3-Bis(2-chloroethyl)-1-nitrosourea but not of 3'-[-3-(2-chloroethyl)-3-nitrosoureidol-3'-deoxythymidine," *Cancer Research* 51: 1586-1590 (1991).

METHOD OF EXTENDING THE VASCULAR DWELL-TIME OF PARTICULATE THERAPEUTIC AND PARTICULATE DIAGNOSTIC AGENTS

TABLE OF CONTENTS

1. Technical Field
2. Background of the Invention
3. Summary of the Invention
4. Detailed Description of the Invention
4.1 The Mode of the Invention
4.2 Mode of Administration
5. Examples
5.1 Biological Data

1. TECHNICAL FIELD

The present invention relates to a method for increasing the vascular dwell-time of a particulate therapeutic or particulate diagnostic agent in a mammal through the adjunct administration of an effective amount of the particulate therapeutic or particulate diagnostic agent and an effective amount of a vascular dwell-time enhancing agent. This method, therefore, provides a means by which a therapeutic or diagnostic agent is capable of expressing its efficacy by remaining within the vascular compartment or being carried within the vascular compartment to a target. Accordingly, this method is particularly well-suited for treating several conditions in a mammal, including hypoxia, hypoxemia, anemia, infection and cancer as well for imaging selected regions within a mammal by various imaging techniques, including ultrasound imaging, X-ray imaging and MRI.

2. BACKGROUND OF THE INVENTION

The efficacy of many therapeutic and diagnostic agents is predicated on the ability of these agents to be retained within the vascular compartment or to be carried within the vascular compartment to their target within a mammal. Unfortunately, many of these agents when they are within the vascular compartment appear particulate in size, as this concept is defined below in Section 4.1. Because these agents activate or prime phagocytes (phagocytic cells) that are present within the vascular compartment and in fixed tissues of the body, they are susceptible to phagocytosis and pinocytosis. The triggering of these two processes in turn results in the accelerated removal of these agents from the vascular compartment. These agents are then stored within the organs of the reticuloendothelial system, as well as other tissues, until they are metabolized or excreted. In this context, the length of time during which these agents are within the vascular compartment, that is, their vascular dwell-time (intravascular persistence), is relatively short. Because these agents display short dwell-times within the vascular compartment, the ability of these agents to express their efficacy is severely compromised.

Furthermore, when the phagocytic response induced by these agents is particularly pronounced, the phagocytes that are present within the vascular compartment and the fixed tissues of the body often trigger a number of secondary responses which, in turn, cause a number of negative side-effects. For example, activation of phagocytes is known to cause the release of cytokines, such as Tumor Necrosis Factor (TNF) and Interleukin I, as well as ecoisanoids, such as Thromboxane $A_2$ and Prostaglandin $E_2$.

These cytokines and ecoisanoids can cause fever, back pain and pulmonary hypertension. See Inflammation: Basic Principles and Clinical Correlates (J. I. Gallin, I. M. Goldstein and R. Snyderman eds. 1988). Similarly, it has been observed that mammals that have received a particulate fluorocarbon suffer from cachexia. Cachexia is the name given to a generally weakened condition of the body or mind resulting from any debilitating chronic disease. Typical symptoms of cachexia include severe weight loss, depression, loss of appetite, anorexia and anemia. Cachexia is normally associated with neoplastic diseases, chronic infectious diseases or thyroiditis, and is a particular problem when associated with cancerous conditions. In particular, cachexia often compromises a mammal's response to chemotherapy and radiotherapy. This condition, in particular, is believed to be induced by the secretion of the cytokine TNF. See Tracey, K. J. et al. "Cachectin/Tumor Necrosis Factor Induces Cachexia, Anemia, Inflammation," *J. Exp. Med.* 167:1211–1227 (1988).

Traditionally, the obstacles posed by increased phagocytic activity have been overcome by the sophisticated regulation of a number of parameters, including the regulation of the size of these agents, the dosage employed, the rate of infusion and the frequency with which these agents are administered.

In this context, there is need within the art to extend the vascular dwell-time of these agents and, therefore, counter the effects of phagocytosis, by methods that are not predicated on the intricate regulation of the aforementioned parameters.

3. SUMMARY OF INVENTION

The instant invention relates to a novel method by which the vascular dwell-time of a particulate therapeutic or particulate diagnostic agent can be enhanced. The method comprises the adjunct administration of a particulate therapeutic or particulate diagnostic agent and a vascular dwell-time enhancing agent, as the term is defined in Section 4.1, to a mammal.

Accordingly, the invention relates to a method for delivering a particulate therapeutic or particulate diagnostic agent by means of the vascular compartment of a mammal which comprises the adjunct administration of an effective amount of the particulate therapeutic or particulate diagnostic agent and an effective amount of a vascular dwell-time enhancing agent to a mammal.

The present invention further relates to a method for preventing or treating several mammalian conditions, in particular, hypoxia, hypoxemia and anemia. This method comprises the adjunct administration of a therapeutically effective amount of a particulate blood substitute and an effective amount of a vascular dwell-time enhancing agent to a mammal in need of said prevention or treatment.

The present invention also relates to a method for treating a neoplastic condition in a mammal which comprises irradiating a tumor cell in the mammal at least about three hours after the adjunct administration of a therapeutically effective amount of a particulate blood substitute and an effective amount of a vascular dwell-time enhancing agent to the mammal.

Furthermore, the present invention relates to a method for imaging a selected tissue or organ of a mammal which comprises imaging the tissue or organ after the mammal has received an adjunct administration of an effective amount of a particulate imaging agent and an effective amount of a vascular dwell-time enhancing agent.

In addition, the present invention relates to a method for preventing or treating cachexia in a mammal which comprises the administration of an anti-cachexia agent to a mammal in need of said prevention or treatment.

The present invention also relates to a composition comprising a particulate therapeutic or a particulate diagnostic agent and a vascular dwell-time enhancing agent.

Finally, the present invention relates to a kit comprising:

1) a vascular dwell-time enhancing agent associated with a carrier system; and 2) either a particulate therapeutic agent or a particulate diagnostic agent.

4. DETAILED DESCRIPTION OF THE INVENTION

4.1 The Method of the Invention

Based on the adjunct administration of the vascular dwell-time enhancing agents of the instant invention, the instant invention provides greater flexibility in counteracting the effects of phagocytosis and pinocytosis. In particular, the traditional approaches employed for regulating these effects (the size of the particulate therapeutic or particulate diagnostic agent, the dosage employed, the rate of infusion as well as the frequency with which the particulate therapeutic or particulate diagnostic agent is administered) have taken on diminished importance with respect to preventing the activation of phagocytes.

In fact, based on the manner in which phagocytosis and pinocytosis are suppressed by these vascular dwell-time enhancing agents, it is believed that greater dosages of the particulate therapeutic and particulate diagnostic agent can be administered over a shorter period of time than could be previously achieved. In addition, it is believed that once the effects of these vascular dwell-time enhancing agents wear off, a heightened phagocytic response does not ensue. As a result, it is believed that vascular dwell-time enhancing agents may be affecting the metabolic action of cytokines and ecoisanoids, as well as the onset of the negative side effects they trigger.

Finally, when such vascular dwell-time enhancing agents are adjunctively administered with a particulate therapeutic or particulate diagnostic agent, the biodistribution as well as the biodegradability of the latter may be significantly enhanced. For example, when the particulate therapeutic or particulate diagnostic agent is a fluorocarbon, it has been found that significantly lower levels of the particulate fluorocarbon accumulate within the organs of the reticuloendothelial system (the liver, spleen, lung and bone marrow) until the particulate fluorocarbon is metabolized or excreted. Instead, based on the adjunct administration of a vascular dwell-time enhancing agent, it has been discovered that greater levels of the particulate fluorocarbon remain within the vascular compartment. Eventually, the particulate fluorocarbon is excreted through the lungs after the particulate fluorocarbon has served its intended function.

While not being bound by theory, it is believed that the beneficial effects of these vascular dwell-time enhancing agents relate to the manner in which carrier systems, to which the therapeutic and diagnostic agents are associated, are metabolized. Often therapeutic and diagnostic agents are formulated in carrier systems, such as lipids, lipid emulsions or liposomal systems before they are administered in order for example to, increase the tolerance of the therapeutic or diagnostic agent within the vascular compartment. In addition, it is believed that the body will often associate the therapeutic and diagnostic agents with a carrier system once the therapeutic and diagnostic agents are administered. In fact, this phenomenon can occur regardless of whether the therapeutic or diagnostic agents are formulated with a carrier system prior to administration.

In this context, it is the carrier system to which the therapeutic or diagnostic agents are associated after administration that renders the therapeutic or diagnostic agents susceptible to phagocytosis and macrophage activity. Accordingly, it is believed that the vascular dwell-time enhancing agents protect the carrier system to which the therapeutic or diagnostic agents are associated after administration from being metabolized or that the vascular dwell-time enhancing agents activate those lipid metabolic processes that, in turn, enhance the stability of the carrier system to which the therapeutic or diagnostic agents are associated after administration. Thus, the enhanced stability of the carrier system, in turn, renders the therapeutic and diagnostic agents less susceptible to phagocytosis and macrophage activity.

Alternatively, it is believed that the vascular dwell-time enhancing agents may correct the abnormal metabolism of the carrier systems, which often results from the production of cytokines or ecoisanoids. For example, one possible mechanism of action could be the down-regulation of cytokine and ecoisanoid production.

A particularly likely theory is that the increase in vascular dwell-time is related to the ability of the vascular dwell-time enhancing agents to inhibit the activity of at least one of the following enzymes: AND glycohydrolase (NADase), ADP-ribose-synthetase or ADP-ribose-polymerase. The latter two enzymes are believed to repair cells attacked by cytokines such as TNF. This hypothesis has been supported experimentally. In particular, it has been found that nicotinamide, a compound that is believed not only to inhibit activity of the three aforementioned enzymes but also to stimulate cell repair in damaged cells, is useful in preventing and treating cachexia. Thus, agents that inhibit NADase, ADP-ribose-synthetase or ADP-ribose polymerase activity can be used not only to increase vascular dwell-time but also to treat or prevent cachexia.

In this vein, suitable particulate therapeutic and particulate diagnostic agents of the instant invention are those therapeutics and diagnostics which, given the form in which they are administered to a mammal, activate the phagocytes present within the vascular compartment or in the fixed tissues of the body and in turn are cleared from the vascular compartment by phagocytosis or pinocytosis.

The preferred mammal of interest, of course, is the human. Nonetheless, other preferred mammals include domesticated mammals such as equine, bovine, ovine, porcine, canine, feline, feline and murine species.

The terms "particulate therapeutic" and "particulate diagnostic," refer to any therapeutic and diagnostic agent that is known or to be developed and that, after being administered, would be capable of activating the phagocytes of the vascular compartment or the fixed tissues of the body. Accordingly, these two terms refer to those therapeutic and diagnostic agents that, on their own are capable of activating these phagocytes. In addition, these two terms refer to those agents that, because of their association with a carrier system within the body, would be capable of activating these phagocytes. Typically, these agents measure from about 0.02 to about 10 microns in diameter and more typically from about 0.05 microns to about 1 micron in diameter. Generally speaking, phagocytes are activated when a particle within the vascular compartment measures from about 0.001 to about 50 microns in diameter.

Suitable carrier systems to which the therapeutic or diagnostic agents can be associated include lipids, liposomes, microspheres, molecules to which the therapeutic or diagnostic agent is conjugated or cross-linked, artificial cells, microcapsules, microcarrier beads as well as any other carrier system known to one of ordinary skill in the art or to be developed in the future, so long as the result is a particulate therapeutic agent or a particulate diagnostic agent.

With respect to suitable vascular dwell-time enhancing agents, it has been surprisingly discovered that lipid metabolism modifying agents, certain antibiotics, cyclooxogenase inhibitors, NADase inhibitors, ADP-ribose-polymerase inhibitors and ADP-ribose-synthetase inhibitors are capable of extending the vascular dwell-time of a particulate therapeutic or a particulate diagnostic agent so that the latter class of agents is, in turn, more capable of expressing its efficacy.

The term "lipid metabolism modifying agents" refers to those agents which, when introduced to a mammal, are capable of modulating the synthesis or activity of at least one key lipogenic enzyme. A lipogenic enzyme is an enzyme that is capable of influencing the generation of lipids in fats. Non-limiting examples of such enzymes include lipoprotein lipase, membrane lipase, phospholipase $A_2$ and 3-hydroxy-3-methylglutaryl-coenzyme A (HMG-CoA) reductase. Accordingly, any agent that is known or to be developed and which falls within this definition can be utilized in the instant invention.

Non-limiting examples of lipid metabolism modifying agents include: clofibrate; gemfibrizol; probucol; thyroxin; insulin; lovastatin; nicotinic acid; and nicotinamide (niacinamide). Preferred lipid metabolism modifying agents are nicotinamide and nicotinic acid, with nicotinamide being more preferred.

Suitable antibiotics are those antibiotics known or to be discovered that are derived from the following sources: Streptomyces, *Bacillis subtilis, Cephalosporin acremonium*, as well as variants of *Micromonospora purpurea* and *Micromonospora echinospora*.

Non-limiting examples of antibiotics derived from Streptomyces include neomycin, streptomycin, kanamycin, paromomycin, novobiocin, vancomycin, lincomycin, oleandomycin, chloramphenicol, clindamycin, cefoxitin, amphotericin B, tobramycin and amikacin. A non-limiting example of an antibiotic derived from Bacillis subtilis is bacitracin. Non-limiting examples of antibiotics derived from Cepahalosporin acremonium include: cephalosporin C and semisynthetic antibiotic derivatives of cephalosporin C. A non-limiting example of an antibiotic derived from Micromonospora purpurea, Micromonospora echinospora or a variant of these two strains is gentamicin. Of these antibiotics, the preferred antibiotic is neomycin. It is important to note that the invention does not require that these antibiotics be derived from the aforementioned natural sources. As a result, the invention encompasses these antibiotics regardless of how they are made.

The vascular dwell-time enhancing agent can also be any cyclooxogenase inhibitor, known or to be discovered in the future, with the preferred cyclooxogenase inhibitor being ibuprofen.

Of all these classes of vascular dwell-time enhancing agents, however, the lipid metabolism modifying agents and the antibiotics are preferred, with the lipid metabolism modifying agents being more preferred.

Other non-limiting examples of compounds which are useful as vascular dwell-time enhancing agents include: thymine, thymine analogs such as thymine riboside and thymidine, theophylline, benzamide, as well as benzamide analogs and nicotinamide analogs such as 3-aminobenzamide, benzoic acid, 3-amino-benzoic acid and α-amino-3-indolepropionic acid, AND, NADH, and NADPH.

Because the vascular dwell-time enhancing agents, when administered adjunctively, are capable of extending the vascular dwell-time of a particulate therapeutic or a particulate diagnostic agent, the present invention provides an advantageous method for delivering a particulate therapeutic or a particulate diagnostic by means of the vascular compartment of a mammal.

For example, the vascular dwell-time enhancing agents can be instrumental to ensuring that particulate therapeutic agents, such as particulate antibiotics, particulate chemotherapeutics, particulate vasopressors, particulate anti-inflammatory agents, particulate sedatives, particulate anesthetics, particulate tranquilizers, particulate soporifics and particulate vasodilators, and particulate diagnostics, such as particulate antibodies and particulate radiolabelled compounds, are more capable of exhibiting their efficacy.

In a preferred embodiment, the vascular dwell-time enhancing agents are adjunctively administered with a particulate blood substitute in order to treat conditions such as anemia, hypoxia or hypoxemia. These conditions are often brought about by disorders such as hemorrhagic shock, sepsis, trauma and myocardial infarction.

In addition, the vascular dwell-time enhancing agents of the present invention can be administered with a particulate blood substitute to prevent the onset of these conditions. In this context, the administration of the particulate blood substitute has a prophylactic effect whereby hypoxia, hypoxemia and anemia are prevented. Accordingly, the vascular dwell-time enhancing agent and particulate blood substitute can be administered during any surgical procedure in which blood circulation and perfusion are compromised. Such procedures include angioplasty as well as cardiopulmonary bypass surgery. Thus, in appropriate circumstances, the two agents can be administered via a cell sorting machine or heart-lung machine pump.

Similarly, in another embodiment of the invention, the adjunctive administration of a vascular dwell-time enhancing agent and a particulate blood substitute is incorporated into a regime designed to treat a neoplastic condition. Based on the increased dwell-time of the particulate blood substitute within the vascular compartment, neoplastic tissue has a greater chance of up-taking oxygen. This phenomenon, in turn, renders such tissue vulnerable to the effects of radiation therapy, chemotherapy and hyperthermia therapy.

In fact, the effects of these agents are so great that a mammal can receive multiple treatments of the therapy based on a single dosage of the particulate blood substitute. Accordingly, the need to re-administer the particulate blood substitute for subsequent treatments is unnecessary. Furthermore, the instant embodiment reduces the toxicological concerns triggered by administering successive dosages of a particulate blood substitute to a mammal.

With respect to radiation treatment, in particular, the effects of the vascular dwell-time enhancing agents are so dramatic that the neoplastic tissue need not receive radiation treatment directly following the adjunct administration of the two agents. Typically, radiation treatment can be administered at least about 3 hours after the adjunct administration of the two agents. While radiation can even be applied about 72 hours after the adjunct administration of the two agents, it is preferred that radiation treatment commence within about the first 3 hours to about 48 hours of the adjunct administration of the two agents.

For each of the embodiments discussed in this Section relating to blood substitutes, any particulate blood substitute known or to be developed can be utilized. Non-limiting examples of particulate blood substitutes include hemoglobin based compositions, such as hemoglobin that has been cross-linked or otherwise polymerized as well as hemoglobin that has been formulated prior to administration with a carrier system, as the latter term has been previously defined in this Section.

In addition, a fluorocarbon, which includes any compound containing a fluorocarbon hydrocarbon moiety, can be used as a blood substitute. Non-limiting examples of fluorocarbons include:

1) a bis(F-alkyl)ethanes, such as $CH_4F_9CH=CHC_4F_9$ (F-44E), i-$C_3F_7CH=CHC_6F_{13}$ (F-i36E) and $C_6F_{13}CH=CHC_6F_{13}$ (F-66E), $C_3F_7CBr=CBrC_3F_7$, $C_3F_7CI=CIC_3F_7$, $C_2F_5CBR=CbrC_2F_5$, $C_2F_5CI=CIC_2F_5$;

2) cyclic fluorocarbons, such as $C_{10}F_{18}$ (FDC), F-adamantane (FA), F-methyladamantane (FMA), F-1,3-dimethyladamantane (FDMA), F-di- or F-trimethyl-bicyclo[3,3,1]nonane (nonane);

3) perfluorinated amines, such as F-tripropylamine (FTPA) F-tributylamine (FTBA), F-4-methylocytlhydroquinolizine (FMOQ), F-n-methyl-decahydroisoquinoline (FMIQ), F-n-methyldecahydroquinoline (FHQ), F-n-cyclohexylpyrrolidine (FCHP) and F-2-butyltetrahydrofuran (FC-75 or RM101);

4) halogenated perfluorocarbons, such as:
   i) monobrominated perfluorocarbons, such as 1-bromoheptadecaflourooctane (PFOB), 1-bromopentadecaflouroheptane, 1-bromotridecafluorohexane (PFHB);
   ii) dibrominated perflurorocarbons, such as $C_6F_{12}Br_2$, $C_7F_{14}Br_2$ and $C_8F_{16}Br_2$;
   iii) monoiodiniated perfluorocarbons;
   iv) di-iodinated perfluorocarbons;

5) perfluoroalkylated ethers or polyethers, such as $(CF_3)_2CFO(CF_2CF_2)_2OCF(CF_3)_2$, $(CF_3)_2CFO(CF_2CF_2)_3OCF(CF_3)$, $(CF_3)_2CFO(CF_2CF_2)_2F$, $(CF_3)_2CFO(CF_2CF_2)_3F$, $(C_6F_{13})_2O$ and $F[CF(CF)CFO]CHFCF$;

6) perfluorocyclic ethers;

7) perfluoroalkylated hydrides, such as perfluorooctylhydride, perfluorononylhydride; and perfluorodecylhydride; and 8) fluorocarbon-hydrocarbons, such as $C_8F_{17}C_2H_5$ $C_6F_{13}CH=CH_6H_{13}$ and $C_8F_{17}R$, wherein R is any hydrocarbon with an organic functional group.

In another embodiment of the present invention, a vascular dwell-time enhancing agent can be administered adjunctively with a particulate contrast agent to image a particular tissue or organ of interest. Non-limiting examples of such imaging techniques include ultrasound imaging, X-ray imaging (such as computed axial tomography imaging (CAT)), and magnetic resonance imaging (MRI).

By virtue of these imaging techniques, valuable diagnostic information can be gathered regarding various tissues, organs and systems within a mammal. Accordingly, these techniques can be used to gather information about the heart, blood as well as the lymphatic system and the vascular compartment. Furthermore, because a sufficient amount of the particulate diagnostic agent still accumulates within the reticuloendothelial system, the liver, lung, spleen and bone marrow of a mammal can also be imaged. With respect to the liver and spleen, these techniques are particularly well suited for detecting tumors and lesions.

Suitable particulate ultrasound contrast agents include proteinaceous matrices containing oxygen, air or another gas, such as oxygen embedded albumin microspheres, as well as fluorocarbons, such as those previously recited in this Section.

Suitable particulate X-ray contrast agents are compounds that have been labeled with a heavy halogen, such as iodine and bromine, including the monobrominated, dibrominated, monoiodinated and diiodinated fluorocarbons previously identified in this Section.

Finally, suitable particulate MRI contrast agents include: paramagnetic compounds, such as ferric oxyhydroxide, gadolinium oxide, and fluorocarbons, such as those identified previously; ferromagnetic compounds, such as magnetite, ferrite and gamma ferric oxide; and superparamagnetic compounds, such as superparamagnetic iron oxide.

Because the vascular dwell-time of the particulate therapeutic or particulate diagnostic agent is enhanced, the biodistribution and ultimate fate of the agents within the mammal can be dramatically effected as well. For example, with respect to fluorocarbons, greater levels of the fluorocarbons are present in the vascular compartment. Ultimately, the fluorocarbons are expired across the pulmonary membrane as a gas through the lungs.

Another aspect of the present invention is that many of the vascular dwell-time enhancing agents, as well as agents that are not vascular dwell-time enhancing agents, can be administered to a mammal in order to prevent or treat cachexia. These agents are termed anti-cachexia agents. Accordingly, the anti-cachexia agents can treat or prevent effects conventionally associated with cachexia, such as weight loss, depression, loss of appetite, lipid metabolic disorders, piloerection and decreased responses to chemotherapy and radiotherapy.

Suitable anti-cachexia agents include those agents that are known or to be discovered and that are capable of inhibiting NADase, ADP-ribose-synthetase or ADP-ribose-polymerase activity in a mammal. Typically, the anti-cachexia agents also stimulate DNA repair in damaged cells in a mammal. In this light, a preferred anti-cachexia agent is one that can effect all four of these previously mentioned metabolic mechanisms.

Non-limiting examples of anti-cachexia agents include: thymine, thymine analogs such as thymine riboside and thymidine, theophylline, nicotinamide, benzamide, as well as, nicotinamide analogs and benzamide analogs such as nicotinic acid, 3-aminobenzamide, benzoic acid, 3-amino-benzoic acid, and α-amino-3-indolepropionic acid, AND, NADH and NADPH.

4 2. Mode of Administration

The instant invention, in part, comprises the adjunct administration of a vascular dwell-time enhancing agent and a particulate therapeutic or a particulate diagnostic agent. In this context, the term "adjunct administration" means that these two agents can be administered to a mammal either as a mixture or, sequentially, so long as the first agent to be administered is still capable of serving its intended function within the mammal when the second agent is administered.

With respect to the particulate therapeutic or particulate diagnostic agent, this agent can be formulated and administered in accordance with those methods traditionally employed within the art as well as those known to one of ordinary skill in the art. Given the benefits of the vascular dwell-time enhancing agents, however, the conventional dosages and perfusion rates required to counter the effects of phagocytosis may no longer be necessary; for, it is believed that a greater dosage can now be administered over a shorter time. The degree to which adjustments in the dosages and doses to be administration may be required can be readily determined by one of ordinary skill in the art. Accordingly, the term "effective amount of a therapeutic or diagnostic agent" refers to a therapeutically effective amount of a particulate therapeutic agent and a diagnostically effective amount of a particulate diagnostic agent respectively.

Ideally, the vascular dwell-time enhancing agent and the particulate therapeutic or particulate diagnostic agent are packaged in the form of kit which contains an effective amount of a vascular dwell-time enhancing agent and an effective amount of the particulate therapeutic or particulate diagnostic agent. These agents can be packaged so that they can be administered in accordance with any of the regimes and methods mentioned in the following discussion.

With respect to the vascular dwell-time enhancing agents in general, these agents can be formulated together with the particulate therapeutic or particulate diagnostic agent. In addition, these agents can be formulated separately and subsequently mixed with the particulate therapeutic or particulate diagnostic agent. In either instance, however, both agents can be administered as a mixture.

When the vascular dwell-time enhancing agents are formulated with the particulate therapeutic or particulate diagnostic agent, it is preferred that an initial bolus injection of the vascular dwell-time enhancing agent be administered to a mammal as a primer. This administration is then followed, about 5 minutes to about 4 hours later, by a second administration, comprising a mixture of the vascular dwell-time enhancing agent and a particulate therapeutic or particulate diagnostic agent.

Generally, when this second administration contains a particulate therapeutic agent, the mixture is preferably administered intravenously over a period of time of at least about 15 minutes. Based on the particulate therapeutic being administered, the mixture may require a longer period of administration. The time required for administering a given particulate therapeutic will be readily appreciated by one of ordinary skill in the art.

When the second administration contains a particulate diagnostic agent, the mixture is preferably administered intravenously over a period of time of at least about 3 minutes to about 10 minutes.

When administering either a particulate therapeutic or particulate diagnostic agent, additional doses of a vascular dwell-time enhancing agent may be administered. Preferably, these subsequent doses of the vascular dwell-time enhancing agent are administered by an intravenous infusion, an injection or oral ingestion.

When administered separately, the vascular dwell-time enhancing agents and anti-cachexia agents can be administered enterally, that is, orally, topically, by inhalation spray or rectally in dosage unit formulations containing conventional non-toxic pharmaceutically acceptable carrier systems.

In addition, the agents can be administered parenterally, that is by subcutaneous, intravenous, intramuscular, injection or infusion techniques.

As for suitable formulations, the vascular dwell-time enhancing agents and anti-cachexia agents can be formulated in any number of ways, depending on the mode of administration contemplated. For example, when administered orally, the agents can be incorporated into a tablet, troche, lozenge, aqueous or oily suspension, dispersible powder or granule, emulsion, hard or soft capsule, syrup or elixir. Furthermore, these compositions can also contain additional ingredients, such as sweetening agents, flavoring agents, coloring agents or preservatives, in order to provide a more elegant and palatable composition. These compositions can be prepared according to any method known in the art.

When formulated as a tablet, the vascular dwell-time enhancing agents and anti-cachexia agents can be admixed with a non-toxic pharmaceutically acceptable excipient. Suitable excipients are, for example: inert diluents, such as calcium carbonate, sodium carbonate, lactose, calcium phosphate or sodium phosphate; granulating and disintegrating agents, for example, maize starch, or alginic acid; binding agents, for example, starch, gelatin or acacia; and lubricating agents, for example, magnesium stearate, stearic acid or talc.

The tablet can also be uncoated or coated by known techniques in order to delay the disintegration of the tablet and the absorption of the agents by the gastrointestinal tract. As a result, a sustained action over a longer period can be achieved. Suitable time delay agents are glyceryl monostearate and glyceryl disterate.

Formulations for oral use can also be presented as gelatin capsules. When in the form of a hard capsule, the vascular dwell-time enhancing agents and anti-cachexia agents are mixed with an inert solid diluent, for example, calcium carbonate, calcium phosphate or kaolin. As a soft gelatin capsule, the vascular dwell-time enhancing agents are mixed with water or an oil medium, for example, peanut oil, liquid paraffin, or olive oil.

Aqueous suspensions usually contain the vascular dwell-time enhancing agents and anti-cachexia agents in an admixture with appropriate excipients. Such excipients include: suspending agents, for example, sodium carboxymethylcellulose, methylcellulose, hydroxypropylmethylcellulose, sodium alinate, polyvinylpyrrolidone, gum tragacanth and gum acacia; dispersing or wetting agents which can be a naturally occurring phosphatide, for example, lecithin; condensation products of an alkylene oxide with a fatty oxide, for example, polyoxyethylene stearate; condensation products of ethylene oxide with a long chain aliphatic alcohol, for example, heptadecaethyleneoxycetanol; condensation products of ethylene oxide with a partial ester derived from fatty acids and a hexitol such as polyoxyethylene sorbitol monooleate; or condensation products of ethylene oxide with a partial ester derived from fatty acids and hexitol anhydrides, for example, polyoxyethylene sorbitan monooleate.

The aqueous suspensions can also contain additional ingredients, such as: one or more preservatives, for example, ethyl, n-propyl, or p-hydroxybenzoate; coloring agents; flavoring agents; or sweetening agents, such as sucrose or saccharin.

Oily suspensions can be formulated by suspending the vascular dwell-time enhancing agents in a vegetable oil, for example, arachis oil, olive oil, sesame oil or coconut oil; or in a mineral oil, such as liquid paraffin. These suspensions can contain a thickening agent, for example, beeswax, hard paraffin or cetyl alcohol. Sweetening agents, such as those set forth above, and flavoring agents can be added to provide a palatable oral preparation. Furthermore, these compositions can be preserved by the addition of an antioxidant, such as ascorbic acid.

Powders and granules can also be dispersed in an aqueous suspension by the addition of water, a dispersing or wetting agent, and, optionally, one or more preservatives. Suitable dispersing agents, wetting agents and suspending agents are exemplified by those already mentioned in this Section. Additional excipients, for example, sweetening, flavoring and coloring agents, can also be present.

The vascular dwell-time enhancing agents and anti-cachexia agents can also be prepared in oil-in-water emulsions. The oily phase can be a vegetable oil, for example, olive oil or arachis oils, or a mineral oil, for example, liquid paraffin or mixtures of these. Suitable emulsifying agents can be naturally-occurring gums, for example: gum acacia or gum tragacanth; naturally-occurring phosphatides, for example, soybean lecithin; esters including partial esters derived from fatty acids and hexitol anhydrides, for example, sorbitan mono-oleate; and condensation products of said partial esters with ethylene oxide, for example, polyoxyethylene sorbitan mono-oleate. The emulsions can also contain sweetening and flavoring agents.

Syrups and elixirs can be formulated with sweetening agents, for example glycerol, sorbitol or sucrose. Such formulations can contain a demulcent, as well as a preservative, flavoring agent or coloring agent.

The vascular dwell-time enhancing agents and anti-cachexia agents also can be in the form of sterile injectable aqueous or oleaginous suspensions. These suspensions can be formulated by those general techniques known in the art and using suitable dispersing or wetting agents and suspending agents which have been mentioned in this Section. The sterile injectable preparation can be a sterile injectable solution or suspension in a non-toxic parenterally acceptable diluent or solvent. Among the acceptable diluents and solvents that can be employed are water, 1,3-butanediol, Ringers solution and isotonic sodium chloride solution.

In addition, sterile fixed oils are conventionally employed as a solvent or suspending medium. For this purpose any bland fixed oil can be employed including synthetic mono- or diglycerides. Fatty acids such as oleic acid also find use in the preparation of injectables.

The vascular dwell-time enhancing agents and anti-cachexia agents can also be in the form of suppositories for rectal administration. These compositions can be prepared by mixing the agents with a suitable non-irritating excipient which is solid at ordinary temperatures and liquid at the rectal temperature. As a result, the excipient will melt and release the agents in the rectum. Suitable excipients include cocoa butter and polyethylene glycols.

When these agents are administered on their own, they are preferably formulated in a carrier system, non-limiting examples of which have previously been recited in Section 4.1. By administering the vascular dwell-time enhancing agents or anti-cachexia agents in such a manner, one is capable of delivering the agents to specific targets within a mammal, such as the phagocytes present within the vascular compartment or fixed tissue of the mammal. As a result, very high doses of the agents are delivered to the target while very low doses are delivered to the rest of the mammal.

When these agents are not formulated in a carrier system and are administered separately, they are preferably administered in the following manner: when these agents are administered enterally, they are preferably administered orally in 3–4 dosages per day. When these agents are administered parenterally, they are preferably administered in a manner similar to that discussed previously in this Section. First, an initial bolus injection of these agents is administered. Three to four hours later, the agents are intravenously administered over a 24 hour period. Subsequent 24 hour dosages are repeated until the efficacy of these agents is no longer required.

With respect to the dosage levels to be administered, the dosage level should be generally from about 5 mg/kg per day to about 1,000 mg/kg per day. Ultimately the object of administering these vascular dwell-time enhancing agents and anti-cachexia agents is to maximize either the concentration of the particulate therapeutic agent or particularte diagnostic agent in the blood, or to maximize the appetite and activity of the mammalian subject over a given period of time respectively. At the same time, however, one should strive to apply as low a dose of the vascular dwell-time enhancing agents and anti-cachexia agents as possible and to maintain a constant concentration of these agents within the blood as long as their efficacy is required. Prolonged use of these agents at the lower dosage range recited above should not be problematic given the relatively low toxicity of these agents.

For example, when nicotinamide is administered orally, the dosage should be about 500 mg/kg/day. When nicotinamide is administered by the preferred parenteral mode, an initial bolus injection of about 500 mg/kg should be followed by an intravenous administration of about 500 mg/kg/day.

When neomycin is administered orally, the dosage should be about 30 mg/kg/day to about 50 mg/kg/day. When neomycin is administered by the preferred parenteral mode, an initial bolus injection of about 5 mg/kg should be followed by an intravenous administration of about 5 mg/kg/day to about 10 mg/kg/day.

When ibuprofen is administered orally, the dosage should be about 10 mg/kg/day to about 40 mg/kg/day. When ibuprofen is administered by the preferred parenteral mode, an initial bolus injection of about 10 mg/kg should be followed by an intravenous administration of about 10 mg/kg/day to 40 mg/kg/day.

When isoniazid is administered orally, the dosage should be about 10 mg/kg/day to about 40 mg/kg/day, When isoniazid is administered by the preferred parenteral mode, an initial bolus injection of about 10 mg/kg should be followed by an intravenous administration of about 10 mg/kg to about 40 mg/kg/day.

When nicotinic acid is administered orally, the dosage should be about 500 mg/kg/day. When nicotinic acid is administered by the preferred parenteral mode, an initial bolus injection of about 500 mg/kg should be followed by an intravenous administration of about 500 mg/kg/day.

5. EXAMPLES

5.1 BIOLOGICAL DATA

EXAMPLE I

The Effects of Vascular Dwell-Time Enhancing Agents on the Biodistribution of Perfluorooctylbromide (PFOB)

Four experiments were conducted in order to assess the ability of a vascular dwell-time enhancing agent to extend the dwell-time of a particulate therapeutic or diagnostic agent within the vascular compartment. Two experiments focused on the effects of nicotinamide on the concentration of perfluorooctylbromide (PFOB) in various organs of healthy mice as well as mice with either mammary or colon tumors. The first of these experiments also focused on the ability of neomycin to increase the concentration of PFOB in the blood of mice with mammary tumors. A third experiment compared the effects of nicotinamide with three other vascular dwell-time enhancing agents: isoniazid, nicotinic acid and neomycin. A fourth experiment focused on the effects of ibuprofen on the concentration of PFOB in the blood of healty mice as well as mice with mammary tumors or Lewis lung tumors.

MATERIALS AND METHODS

Mammals

Female Balb/C normal healthy mice as well as female mice bearing mammary, colon or Lewis lung tumors were employed in these studies. Each mouse weighed approximately 20 gm.

Drugs

Perfluorooctylbromide (PFOB) (with a mean particle size of 250 nanometers) was procured from Alliance Pharmaceutical Corp. and administered intravenously as an emulsion (90 gm/100 ml) in the tail vein.

Nicotinamide (Sigma) isoniazid (Sigma), nicotinic acid (Sigma) neomycin (Sigma) solutions were freshly prepared before each experiment. These compounds were dissolved in water and administered intravenously. Ibuprofen (Upjohn Co.) was obtained as sterile stable solution suitable for intravenous administration.

Normal Saline (0.9% w/v) was administered intravenously in the tail vein.

Extraction Techniques

Blood was thawed and a 50 μl sample was removed and mixed with 2 ml of water to lyse the cells. To that sample, 5 ml of ethanol was added in order to break up the emulsion. Twenty minutes later, 20 ml of isooctane was added to the sample in order to extract the fluorocarbon. The treated sample was then mixed thoroughly and centrifuged at 15000 rpm for 12 min. A sample of the resulting supernatant was then removed for analysis. Tissue samples were subject to a modified version of this protocol, in which, prior to the addition of ethanol, tissue samples were thawed, minced and then homogenized in 2 ml of water.

Gas Chromatography Analysis

The gas chromatograph was standardized daily by running standard curves with known concentrations of PFOB. Samples were loaded into the machine and subjected to analysis with an electron capture detector. The PFOB concentration was then calculated from the following equation: [PFOB]=(the area under the chromatograph)×(the slope of the standard curve)×(-the intercept)×(milliliters solvent per gram of tissue or organ).

EXPERIMENT 1

In one experiment, mice were administered intravenously a single dose of PFOB (9 gm/kg). In addition, mice received one of the following: one of three doses of nicotinamide (100 mg/kg, 500 mg/kg, 1000 mg/kg with a rate of perfusion of about 10 ml/kg/min to 20 ml/kg/min); a dose of neomycin (5 mg/kg with a rate of perfusion of about 10 ml/kg/min to 20 ml/kg/min); or a single dose of saline control. The saline control (equivalent in volume to a dose of 1 gm/kg of nicotinamide) was administered by bolus injection or at a rate of perfusion of 10 ml/kg/min. Twenty-four hours post injection, the mice were sacrificed by cervical dislocation. Two milliliters of whole blood were stored in a heparinized tube and frozen (−70° C.) until analysis. At least 20 μl, ideally 50 μl, of bone marrow were frozen (−70° C.) until analysis. The liver, spleen and lung were removed in toto and frozen (−70° C.). Specimens of adipose tissue were also removed. The results of these experiments appear in Tables I and VI.

EXPERIMENT 2

In a second experiment, mice were administered a single intravenous dose of PFOB (10 g/kg with a rate of perfusion of about 10 ml/kg/min. to 20 ml/kg/min.) and either one, two, or three bolus doses (1 gm/kg each) of nicotinamide intraperitoneally or a single (0.01 ml/kg) dose of normal saline control (as in Experiment 1). Forty-eight hours post injection, the mice were sacrificed by cervical dislocation. The spleen, liver, lung and blood were isolated as in Experiment 1. The results of this experiment appears in Tables VII to IX.

EXPERIMENT 3

In a third experiment, mice were administered three bolus doses of a vascular dwell-time enhancing agent intraperitoneally. Nicotinamide was administered at a dose of 500 mg/kg, isoniazid was administered at a dose of 10 mg/kg and neomycin was administered at a dose of 5 mg/kg. Forty-eight hours post injection of PFOB, the mice were sacrificed by cervical dislocation. Blood samples and tissue samples were obtained as in Experiment 1. The results of this experiment appear in Tables X to XIV.

EXPERIMENT 4

In a fourth experiment, mice were administered three bolus doses of ibuprofen (10 mg/kg) intraperitoneally and a single intravenous bolus dose of PFOB (10 g/kg). Forty-eight hours post injection of PFOB, the mice were sacrificed by cervical dislocation. Blood samples were obtained as in Experiment 1. The results of this experiment are summarized in Table XV.

TABLE I

The Concentration of PFOB (mg/g) in the Blood 24 Hours after a Single Dose of Nicotinamide or Neomycin.

| | Mean | S.D.[a] | S.E.[b] | N[c] | p Value[d] | % Change |
|---|---|---|---|---|---|---|
| NORMAL MICE | | | | | | |
| Saline Control | 38.53 | 19.71 | 3.94 | 25 | | |
| Nicotinamide: | | | | | | |
| 100 mg/kg | 34.70 | 13.77 | 2.75 | 25 | <.01 | −19 |
| 500 mg/kg | 37.77 | 13.82 | 2.76 | 25 | >0.1 | −2 |
| 1000 mg/kg | 46.07 | 19.82 | 3.96 | 25 | <.01 | +20 |
| MICE BEARING MAMMARY TUMORS | | | | | | |
| Saline Control | 24.36 | 9.78 | 2.31 | 18 | | |
| Nicotinamide (500 mg/kg) | 29.45 | 7.24 | 1.94 | 14 | <0.05 | +18 |
| Neomycin (5 mg/kg) | 30.45 | 9.47 | 2.30 | 17 | <0.05 | +25 |

TABLE II

The Concentration of PFOB in the Liver 24 Hours after a Single Dose of Nicotinamide.

| | Mean | S.D.[a] | S.E.[b] | N[c] | p Value[d] | % Change |
|---|---|---|---|---|---|---|
| NORMAL MICE | | | | | | |
| Saline Control | 20.38 | 3.20 | 0.64 | 25 | | |
| Nicotinamide: | | | | | | |
| 100 mg/kg | 19.06 | 2.97 | 0.59 | 25 | >0.1 | −7 |
| 500 mg/kg | 18.28 | 2.26 | 0.45 | 25 | <0.005 | −10 |
| 1000 mg/kg | 16.57 | 2.26 | 0.45 | 25 | <0.0005 | −19 |

[a]S.D. refers to the Standard Deviation of the Mean
[b]S.E. refers to the Standard Error to the Mean. S.E. = $S.D.\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor. III and F. Mostetler, eds. 1986). The usual significance level of 0.05 is used with a one-sided Student t-test comparing a saline control therapy under investigation with the results of the other categories of therapy (such as nicotinamide).

TABLE III

The Concentration of PFOB (mg/g) in Bone Marrow 24 Hours after a Single Dose of Nicotinamide.

| | Mean | S.D.[a] | S.E.[b] | N[c] | p Value[d] | % Change |
|---|---|---|---|---|---|---|
| NORMAL MICE | | | | | | |
| Saline Control | 8.73 | 5.66 | 1.13 | 25 | | |
| Nicotinamide: | | | | | | |
| 100 mg/kg | 8.19 | 5.64 | 1.13 | 25 | >0.1 | −7 |
| 500 mg/kg | 6.61 | 4.07 | 0.81 | 25 | >0.05<.1 | −24 |
| 1000 mg/kg | 7.30 | 3.44 | 0.69 | 25 | >0.1 | −16 |

[a]S.D. refers to the Standard Deviation of the Mean
[b]S.E. refers to the Standard Error to the Mean. S.E. = $S.D.\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy under investigation (such as nicotinamide).

TABLE IV

The Concentration of PFOB (mg/g) in the Spleen 24 Hours after a Single Dose of Nicotinamide.

| | Mean | S.D.[a] | S.E.[b] | N[c] | p Value[d] | % Change |
|---|---|---|---|---|---|---|
| NORMAL MICE | | | | | | |
| Saline Control | 15.9 | 14.2 | 2.8 | 25 | | |
| Nicotinamide: | | | | | | |
| 100 mg/kg | 160.1 | 13.7 | 2.8 | 24 | >0.1 | +2 |
| 500 mg/kg | 174.1 | 15.6 | 3.1 | 25 | <.0.005 | +11 |

TABLE IV-continued

The Concentration of PFOB (mg/g) in the Spleen 24 Hours after a Single Dose of Nicotinamide.

| | Mean | S.D.[a] | S.E.[b] | N[c] | p Value[d] | % Change |
|---|---|---|---|---|---|---|
| 1000 mg/kg | 177.0 | 19.7 | 3.9 | 25 | <0.005 | +13 |

[a]S.D. refers to the Standard Deviation of the Mean
[b]S.E. refers to the Standard Error to the Mean. S.E. = $S.D.\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy under investigation with the results of the other categories of therapy (such as nicotinamide).

TABLE V

The Concentration of PFOB (mg/g) in the Lung 24 Hours after a Single Dose of Nicotinamide.

| | Mean | S.D.[a] | S.E.[b] | N[c] | p Value[d] | % Change |
|---|---|---|---|---|---|---|
| NORMAL MICE | | | | | | |
| Saline Control | 19.5 | 5.79 | 1.16 | 25 | | |
| Nicotinamide: | | | | | | |
| 100 mg/kg | 19.97 | 4.17 | 0.83 | 25 | >0.1 | +2 |
| 500 mg/kg | 19.52 | 4.16 | 0.83 | 25 | >0.1 | 0 |
| 1000 mg/kg | 17.84 | 4.22 | 0.84 | 25 | >0.1 | −8.5 |

[a]S.D. refers to the Standard Deviation of the Mean
[b]S.E. refers to the Standard Error to the Mean. S.E. = $S.D.\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy under investigation (such as nicotinamide).

TABLE VI

The Concentration of PFOB (mg/g) in Adipose Tissue 24 Hours after the Administration of PFOB.

| | Mean | S.D.[a] | S.E.[b] | N[c] | p Value[d] | % Change |
|---|---|---|---|---|---|---|
| NORMAL MICE | | | | | | |
| Saline Control | 4.22 | 1.66 | 0.33 | 25 | | |
| Nicotinamide: | | | | | | |
| 100 mg/kg | 5.45 | 1.91 | 0.38 | 25 | >0.1 | +29 |
| 500 mg/kg | 4.0 | 1.54 | 0.31 | 25 | >0.1 | −5 |
| 1000 mg/kg | 4.56 | 1.76 | 0.35 | 25 | >0.1 | +8 |

[a]S.D. refers to the Standard Deviation of the Mean
[b]S.E. refers to the Standard Error to the Mean. S.E. = $S.D.\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy under investigation (such as nicotinamide).

TABLE VII

The Effect Of One, Two or Three 1 gm/kg Doses of Nicotinamide on the Concentration of PFOB (mg/g) in the Blood 48 Hours after the Administration of PFOB

| | Mean | S.D.[a] | S.E.[b] | N[c] | p Value[d] | % Change |
|---|---|---|---|---|---|---|
| NORMAL MICE | | | | | | |
| Saline Control | 14.62 | 7.34 | 2.32 | 10 | | |
| Nicotinamide: | | | | | | |
| 1× | 22.43 | 4.89 | 1.65 | 10 | <0.01 | +53 |
| 2× | 30.47 | 3.40 | 1.08 | 10 | <0.025 | +40 |
| 3× | 24.43 | 4.97 | 1.57 | 10 | <0.005 | +67 |
| MICE BEARING MAMMARY TUMORS | | | | | | |
| Saline Control | 0.56 | 0.51 | 0.16 | 10 | | |
| Nicotinamide: | | | | | | |
| 1×[e] | 2.99 | 3.51 | 0.78 | 20 | <0.005 | +434 |
| 2×[f] | 14.77 | 6.91 | 1.55 | 20 | <0.0005 | +2538 |
| 3×[g] | 18.06 | 11.31 | 2.53 | 20 | <0.0005 | +3125 |

TABLE VII-continued

The Effect Of One, Two or Three 1 gm/kg Doses of Nicotinamide on the Concentration of PFOB (mg/g) in the Blood 48 Hours after the Administration of PFOB

| | Mean | S.D.[a] | S.E.[b] | N[c] | p Value[d] | % Change |
|---|---|---|---|---|---|---|
| MICE BEARING COLON TUMORS | | | | | | |
| Saline Control | 7.42 | 6.61 | 1.55 | 10 | | |
| Nicotinamide: | | | | | | |
| 1× | 5.68 | 4.4 | 1.39 | 10 | >0.1 | −23 |
| 2× | 27.59 | 12.12 | 3.83 | 10 | <0.0005 | +272 |
| 3× | 37.33 | 17.1 | 5.41 | 10 | <0.0005 | +403 |

[a]S.D. refers to the Standard Deviation of the Mean
[b]S.E. refers to the Standard Error to the Mean. S.E. = S.D.$/\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy (such as nicotinamide).
[e]1× reflects that one dose was administered intraperitoneally 30 minutes before the administration of PFOB intravenously.
[f]2× reflects that one dose was administered intraperitoneally 30 minutes before and 3.5 hours after the administration of PFOB intravenously.
[g]3× reflects that one dose was administered intraperitoneally 30 minutes before and 3.5 hours after and 23.5 hours after the administration of PFOB intravenously.

TABLE VIII

The Effect Of One, Two or Three 1 gm/kg Doses of Nicotinamide on the Concentration of PFOB (mg/g) in the Liver 48 Hours after the Administration of PFOB

| | Mean | S.D.[a] | S.E.[b] | N[c] | p Value[d] | % Change |
|---|---|---|---|---|---|---|
| NORMAL HEALTHY MICE | | | | | | |
| Saline Control | 26.06 | 2.89 | 0.91 | 10 | | |
| Nicotinamide: | | | | | | |
| 1× | 23.39 | 2.71 | 0.86 | 10 | <0.025 | −11 |
| 2× | 24.80 | 2.63 | 0.83 | 10 | >0.1 | −5 |
| 3× | 23.33 | 2.23 | 0.71 | 10 | <0.025 | −11 |
| MICE BEARING MAMMARY TUMORS | | | | | | |
| Saline Control | 39.84 | 4.12 | 1.3 | 20 | | |
| Nicotinamide: | | | | | | |
| 1×[e] | 41.56 | 6.84 | 1.53 | 20 | >0.1 | +4 |
| 2×[f] | 37.03 | 3.75 | 0.84 | 20 | <0.05 | −7 |
| 3×[g] | 35.25 | 4.48 | 1.00 | 20 | <0.01 | −12 |
| MICE BEARING COLON TUMORS | | | | | | |
| Saline Control | 36.07 | 6.89 | 2.1 | 10 | | |
| Nicotinamide: | | | | | | |
| 1× | 37.27 | 4.42 | 1.40 | 10 | >0.1 | +3 |
| 2× | 32.60 | 3.90 | 1.23 | 10 | >0.05<−0.1 | −10 |
| 3× | 28.25 | 3.39 | 1.07 | 10 | <0.005 | −30 |

[a]S.D. refers to the Standard Deviation of the Mean
[b]S.E. refers to the Standard Error to the Mean. S.E. = S.D.$/\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy under investigation (such as nicotinamide).
[e]1× reflects that one dose was administered intraperitoneally 30 minutes before the administration of PFOB intravenously.
[f]2× reflects that one dose was administered intraperitoneally 30 minutes before and 3.5 hours after the administration of PFOB intravenously.
[g]3× reflects that one dose was administered intraperitoneally 30 minutes before and 3.5 hours after and 23.5 hours after the administration of PFOB intravenously.

TABLE IX

The Effect Of One, Two or Three 1 gm/kg Doses of Nicotinamide on the Concentration of PFOB (mg/g) in the Spleen 48 Hours after the Administration of PFOB

| | Mean | S.D.[a] | S.E.[b] | N[c] | p Value[d] | % Change |
|---|---|---|---|---|---|---|
| NORMAL HEALTHY MICE | | | | | | |
| Saline Control | 211.6 | 34.3 | 10.8 | 10 | | |
| Nicotinamide: | | | | | | |
| 1× | 204.9 | 15.3 | 4.8 | 10 | >0.1 | −3 |
| 2× | 201.6 | 13.4 | 4.2 | 10 | >0.1 | −5 |
| 3× | 211.3 | 17.4 | 5.5 | 10 | >0.1 | 0 |
| MICE BEARING MAMMARY TUMORS | | | | | | |
| Saline Control | 138.1 | 33.5 | 10.6 | 20 | | |
| Nicotinamide: | | | | | | |
| 1×[e] | 18.45 | 22.8 | 5.1 | 20 | <0.0005 | +33 |
| 2×[f] | 208.2 | 27.4 | 6.1 | 20 | <0.0005 | +51 |
| 3×[g] | 204.8 | 33.2 | 7.4 | 20 | <0.0005 | +48 |
| MICE BEARING COLON TUMORS | | | | | | |
| Saline Control | 165.1 | 32.2 | 10.2 | 10 | | |
| Nicotinamide: | | | | | | |
| 1× | 146.6 | 30.4 | 9.6 | 10 | >0.1 | −11 |
| 2× | 187.4 | 23.0 | 7.2 | 10 | <0.05 | +14 |
| 3× | 195.8 | 18.1 | 5.7 | 10 | <0.01 | +19 |

[a]S.D. refers to the Standard Deviation of the Mean
[b]S.E. refers to the Standard Error to the Mean. S.E. = S.D.$/\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy under investigation (such as nicotinamide, neomycin and isoniazid).
[e]1× reflects that one dose was administered intraperitoneally 30 minutes before the administration of PFOB intravenously.
[f]2× reflects that one dose was administered intraperitoneally 30 minutes before and 3.5 hours after the administration of PFOB intravenously.
[g]3× reflects that one dose was administered intraperitoneally 30 minutes before and 3.5 hours after and 23.5 hours after the administration of PFOB intravenously.

TABLE X

The Effect of Three Doses of a Vascular Dwell-Time Enhancing Agent on the Concentration of PFOB (mg/g) in the Blood 48 Hours after the Administration of PFOB.[1]

| | Mean | S.D.[a] | S.E.[b] | N[c] | p Value[d] | % Change |
|---|---|---|---|---|---|---|
| NORMAL MICE | | | | | | |
| Saline Control | 18.21 | 6.2 | 1.42 | 19 | | |
| Nicotinamide (500 mg/kg) | 25.12 | 5.88 | 1.28 | 21 | 0.005 | +38 |
| Isoniazid (10 mg/kg) | 19.73 | 6.57 | 1.47 | 20 | 0.15 | +8 |
| Neomycin (5 mg/kg) | 19.94 | 7.41 | 1.62 | 21 | 0.15 | +10 |
| MICE WITH MAMMARY TUMORS | | | | | | |
| Saline Control | 3.11 | 3.84 | 1.03 | 14 | | |
| Nicotinamide (500 mg/kg) | 7.82 | 5.55 | 1.48 | 14 | 0.008 | +151 |
| Isoniazid (5 mg/kg) | 2.61 | 1.71 | 0.44 | 15 | 0.15 | −16 |

[1]The vascular dwell-time enhancing agents were intraperitoneally administered 30 minutes before, 3.5 hours after and 24 hours after the intravenous administration of PFOB.
[a]S.D. refers to the Standard Deviation of the Mean
[b]S.E. refers to the Standard Error to the Mean. S.E. = S.D.$/\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy under investigation (such as nicotinamide, neomycin and isoniazid).

TABLE XI

The Effect of Three Doses of a Vascular Dwell-Time Enhancing Agent on the Concentration of PFOB (mg/g) in the Spleen 48 Hours after the Administration of PFOB.[1]

| | Mean | S.D.[a] | S.E.[b] | N[c] | p Value[d] | % Change |
|---|---|---|---|---|---|---|
| NORMAL MICE | | | | | | |

TABLE XI-continued

The Effect of Three Doses of a Vascular Dwell-Time Enhancing Agent on the Concentration of PFOB (mg/g) in the Spleen 48 Hours after the Administration of PFOB.[1]

| | Mean | S.D.[a] | S.E.[b] | N[c] | p Value[d] | % Change |
|---|---|---|---|---|---|---|
| Saline Control | 174.6 | 23.15 | 5.01 | 22 | | |
| Nicotinamide (500 mg/kg) | 190 | 20.97 | 4.47 | 22 | 0.014 | +9 |
| Isoniazid (10 mg/kg) | 174.7 | 32.32 | 6.89 | 22 | 0.15 | +0 |
| Neomycin (5 mg/kg) | 170.1 | 19.6 | 4.18 | 22 | 0.15 | −3 |
| MICE WITH MAMMARY TUMORS | | | | | | |
| Saline Control | 154.8 | 12.4 | 3.3 | 14 | | |
| Nicotinamide (500 mg/kg) | 167.3 | 20.9 | 5.58 | 14 | 0.033 | +8 |
| Isoniazid (10 mg/kg) | 161.4 | 14 | 3.62 | 15 | 0.096 | +4 |

[1]The vascular dwell-time enhancing agents were intraperitoneally administered 30 minutes before, 3.5 hours after and 24 hours after the intravenous administration of PFOB.
[a]S.D. refers to the Standard Deviation of the Mean
[b]S.E. refers to the Standard Error to the Mean. S.E. = $S.D.\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy under investigation with the results of the other categories of therapy (such as nicotinamide).

TABLE XII

The Effect of Three Doses of a Vascular Dwell-Time Enhancing Agent on the Concentration of PFOB (mg/g) in the Liver 48 Hours after the Administration of PFOB.[1]

| | Mean | S.D.[a] | S.E.[b] | N[c] | p Value[d] | % Change |
|---|---|---|---|---|---|---|
| NORMAL MICE | | | | | | |
| Saline Control | 35.08 | 7.22 | 1.54 | 22 | | |
| Nicotinamide (500 mg/kg) | 28.6 | 5.33 | 1.14 | 22 | 0.001 | −19 |
| Isoniazid (10 mg/kg) | 33.22 | 5.65 | 1.2 | 22 | 0.15 | −5 |
| Neomycin (5 mg/kg) | 32.66 | 5.91 | 1.29 | 22 | 0.115 | −7 |
| MICE WITH MAMMARY TUMORS | | | | | | |
| Saline Control | 39.88 | 4.42 | 1.18 | 14 | | |
| Nicotinamide (500 mg/kg) | 37.84 | 3.8 | 1.02 | 14 | 0.1 | −5 |
| Isoniazid (10 mg/kg) | 42.79 | 5.68 | 1.47 | 15 | 0.069 | 7 |

[1]The vascular dwell-time enhancing agents were intraperitoneally administered 30 minutes before, 3.5 hours after and 24 hours after the intravenous administration of PFOB.
[a]S.D. refers to the Standard Deviation of the Mean
[b]S.E. refers to the Standard Error to the Mean. S.E. = $S.D.\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy under investigation (such as nicotinamide, neomycin and isoniazid).

TABLE XIII

The Effect of Three Doses of a Vascular Dwell-Time Enhancing Agent on the Concentration of PFOB (mg/g) in the Lung 48 Hours after the Administration of PFOB.[1]

| | Mean | S.D.[a] | S.E.[b] | N[c] | p Value[d] | % Change |
|---|---|---|---|---|---|---|
| NORMAL MICE | | | | | | |
| Saline Control | 28.45 | 7.84 | 1.67 | 22 | | |
| Nicotinamide (500 mg/kg) | 22.04 | 7.08 | 1.51 | 22 | 0.003 | −23 |
| Isoniazid (10 mg/kg) | 28.19 | 8.79 | 1.87 | 22 | 0.15 | −1 |
| Neomycin (5 mg/kg) | 29.27 | 8.79 | 1.87 | 22 | 0.15 | 3 |
| MICE WITH MAMMARY TUMORS | | | | | | |
| Saline Control | 24.91 | 6.56 | 1.75 | 14 | | |
| Nicotinamide (500 mg/kg) | 15.35 | 2.36 | .063 | 14 | 0.005 | −39 |
| Isoniazid (10 mg/kg) | 26.56 | 3.15 | 0.81 | 15 | 0.15 | 7 |

[1]The vascular dwell-time enhancing agents were intraperitoneally administered 30 minutes before, 3.5 hours after and 24 hours after the intravenous administration of PFOB.
[a]S.D. refers to the Standard Deviation of the Mean
[b]S.E. refers to the Standard Error to the Mean. S.E. = $S.D.\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy under investigation (such as nicotinamide, neomycin and isoniazid).

TABLE XIV

The Effect of Three Doses of a Vascular Dwell-Time Enhancing Agent on the Concentration of PFOB (mg/g) in a Mammary Tumor 48 Hours after the Administration of PFOB.[1]

| | Mean | S.D.[a] | S.E.[b] | N[c] | p Value[d] | % Change |
|---|---|---|---|---|---|---|
| MICE WITH MAMMARY TUMORS | | | | | | |
| Saline Control | 6.98 | 1.75 | 0.47 | 14 | | |
| Nicotinamide (500 mg/kg) | 6.01 | 1.59 | 0.43 | 14 | 0.069 | −14 |
| Isoniazid (10 mg/kg) | 5.87 | 1.06 | .027 | 15 | 0.023 | −16 |

[1]The vascular dwell-time enhancing agents were intraperitoneally administered 30 minutes before, 3.5 hours after and 24 hours after the intravenous administration of PFOB.
[a]S.D. refers to the Standard Deviation of the Mean
[b]S.E. refers to the Standard Error to the Mean. S.E. = $S.D.\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy under investigation (such as nicotinamide, neomycin and isoniazid).

TABLE XV

The Effect of Three Doses of Ibuprofen on the Concentration of PFOB (mg/g) in Blood 48 Hours after the Administration of PFOB.[1]

| | Mean | S.E.[b] | N[c] | p Value[d] | % Change |
|---|---|---|---|---|---|
| NORMAL MICE | | | | | |
| Saline Control | 9.38 | 0.71 | 19 | | |
| Ibuprofen | 18.56 | 3.61 | 18 | <.01 | 49 |
| MICE WITH MAMMARY TUMORS | | | | | |
| Saline Control | 0.34 | 0.71 | 19 | | |
| Ibuprofen | 1.94 | 3.61 | 18 | <.05 | 83 |
| MICE WITH LEWIS LUNG TUMORS | | | | | |
| Saline Control | 1.67 | 0.71 | 19 | | |

TABLE XV-continued

The Effect of Three Doses of Ibuprofen on the
Concentration of PFOB (mg/g) in Blood 48 Hours after
the Administration of PFOB.[1]

| | Mean | S.E.[b] | N[c] | p Value[d] | % Change |
|---|---|---|---|---|---|
| Ibuprofen | 4.49 | 3.61 | 18 | <.05 | 63 |

[1]Ibuprofen was administered intraperitoneally 24 hours before, 30 minutes before and 24 hours after the intravenous administration of PFOB.
[a]S.D. refers to the Standard Deviation of the Mean
[b]S.E. refers to the Standard Error to the Mean. S.E. = S.D.$\sqrt{N}$
[c]N refers to the number of mice tested
[d]p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy (such as ibuprofen).

RESULTS AND DISCUSSION

The results of Experiment 1 demonstrate that, as the dosage of nicotinamide increased, the concentration of PFOB within the blood increased as well. With increasing dosages of nicotinamide, decreasing amounts of PFOB concentrated within the bone marrow, liver and lung. Finally, neomycin, in comparison to nicotinamide, was able to increase the concentration of PFOB in the blood of tumor bearing mice to a greater extent. The difference in efficacies of neomycin and nicotinamide, however, was not statistically significant.

The results of Experiment 2 demonstrate that, with successive doses of nicotinamide, the concentration of PFOB with in the blood increased. These effects were most pronounced in mice with mammary or colon tumors.

The concentration of PFOB in the blood of tumor bearing mice was lower than the concentration of PFOB in the blood of normal mice. This depressed level of PFOB in the blood of tumor bearing mice is believed to be due to the fact that the tumors themselves had activated the macrophages of the liver, bone marrow and lung. Accordingly, this priming of the macrophages had enhanced phagocytosis as well as the production of ecoisanoids and cytokines—even before the administration of PFOB.

With respect to normal mice, an increase in the concentration of PFOB in the blood was coupled with a decrease in the concentration of PFOB within the spleen, liver, lung and bone marrow. In mice bearing tumors, however, the concentration of PFOB in the spleen also increased as the concentration of PFOB increased in the blood.

The observed lower levels of PFOB in the spleen of tumor-bearing mice are thought to be due to the suppression of spleen phagocytes. This phenomenon is thought to be due to the enhanced production of cytokines and ecoisanoids by activated macrophages located elsewhere in the reticuloendothelial system of tumor-bearing mice. Accordingly, it is believed that phagocytosis in the spleen increased in tumor bearing mice following the administration of nicotinamide because nicotinamide down-regulated the production of cytokines and ecoisanoids by these other macrophages.

The spleen is an important organ in the immunosuppression against infection. Inhibition of the splenic phagocytes in tumor-bearing mice may contribute to these subjects' lowered resistance to infection. Thus, the administration of megadoses of vascular dwell-time enhancing agents, like nicotinamide, may be useful in overcoming the general immunosuppression seen in subjects with malignant tumors.

The results of Experiment 3 demonstrate that different vascular dwell-time enhancing agents, at different doses, were capable of increasing the concentration of PFOB within the blood while simultaneously lowering the PFOB concentration within other organs, such as the liver. These effects were more pronounced in mice bearing mammary tumors as compared to normal mice. Of the four agents tested, nicotinamide, at its dose, was the most effective agent.

The results of Experiment 4 demonstrate that ibuprofen is also capable of increasing the concentration of PFOB within the blood. As noted previously, the depressed levels of PFOB in the blood of tumor bearing mice is believed to be due to the priming of macrophage activity by the tumors present in these mice. Furthermore, differences in the levels of PFOB in the blood of mice bearing different types of tumors is believed to reflect that different tumors induce different levels of macrophage activity and, hence, different levels of phagocytosis.

CONCLUSION

It has been demonstrated that vascular dwell-time enhancing agents, such as nicotinamide, isoniazid, neomycin and ibuprofen are capable of extending the dwell-time of particulate therapeutic and diagnostic agents, such as PFOB, within the vascular compartment. These results suggest that nicotinamide, isoniazid, neomycin and ibuprofen, as well as other vascular dwell-time enhancing agents, are capable of enhancing the efficacy of a particulate therapeutic or a particulate diagnostic agent by allowing the latter to remain within the vascular compartment or to be carried within the vascular compartment to a target.

EXAMPLE II

The Effects of Nicotinamide, Isoniazid and Neomycin on Weight in Mammals Receiving PFOB One experiment was conducted in order to assess the ability of different vascular-dwell time enhancing agents to prevent weight loss normally induced by the administration of a particulate therapeutic or a particulate diagnostic agent. In particular, this experiment focused on the effects of three agents, nicotinamide, isoniazid and neomycin, on the weight of mice being administered PFOB.

MATERIALS AND METHODS

Mammals

Female Balb/C normal healthy mice as well as female Balb/C mice bearing mammary tumors were employed in this study. Each mouse weighed approximately 20 gm.

Drugs

Perfluorooctylbromide (PFOB) was procured from Alliance Pharmaceutical Corp. and administered intravenously as an emulsion (90 gm/100 ml) in the tail vein.

Nicotinamide (Sigma), isoniazid (Sigma), and neomycin (Sigma) solutions were freshly prepared before each experiment. These compounds were dissolved in water and administered intravenously.

Normal Saline (0.9% w/v) was administered intravenously in the tail vein.

Weight Measurements

The weight of each mouse was recorded prior to the administration of PFOB as well as 48 hours after the administration of PFOB.

EXPERIMENT 1

Mice were administered three bolus doses intraperitoneally of a vascular dwell-time enhancing agent. Nicotinamide was administered at a dose of 500 mg/kg, isoniazid was administered at a dose of 10 mg/kg and neomycin was administered at a dose of 5 mg/kg. Forty-eight hours post injection, the mice were sacrificed by cervical dislocation. The results of this experiment are summarized in Tables XVI to XVII.

TABLE XVI

The Effect of Nicotinamide, Isoniazid and Neomycin on the Body Weight (g) of Normal Mice 48 Hours after the Administrationo of PFOB

|  | Mean at Day O | Net Change at Day 2 | % Change at Day 2 | S.D.$^a$ | S.E.$^b$ | N$^c$ | p Value$^d$ |
|---|---|---|---|---|---|---|---|
| Saline Control | 19.89 | −0.41 | −1.85 | 0.83 | 0.19 | 19 |  |
| Nicotinamide (500 mg/kg) | 19.4 | .00 | 0.00 | 0.62 | 0.14 | 21 | <0.05 |
| Isoniazid (10 mg/kg) | 19.66 | −0.71 | −3.21 | 0.85 | 0.19 | 20 | >0.1 |
| Neomycin (5 mg/kg) | 19.81 | 0.48 | 2.17 | 0.30 | 0.17 | 21 | >0.1 |

$^1$The vascular dwell-time enhancing agents were intraperitoneally administered 30 minutes before, 3.5 hours after and 24 hours after the intravenous administration of PFOB.
$^a$S.D. refers to the Standard Deviation of the Mean
$^b$S.E. refers to the Standard Error to the Mean. S.E. = S.D.$\sqrt{N}$
$^c$N refers to the number of mice tested
$^d$p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy (such as nicotinamide, isoniazid and neomycin).

TABLE XVII

The Effect of Nicotinamide and Isoniazid on the Body Weight (g) of Mice Bearing Mammary Tumors 48 Hours after the Administrationo of PFOB

|  | Mean at Day O | Net Change at Day 2 | % Change at Day 2 | S.D.$^a$ | S.E.$^b$ | N$^c$ | p Value$^d$ |
|---|---|---|---|---|---|---|---|
| Saline Control | 22.1 | −0.03 | −0.14 | 0.41 | 0.11 | 14 |  |
| Nicotinamide (500 mg/kg) | 22.99 | 0.46 | 2.08 | 0.69 | 0.18 | 14 | <0.025 |
| Isoniazid (10 mg/kg) | 21.87 | −0.17 | −0.77 | 0.42 | 0.11 | 15 | >.1 |

$^1$The vascular dwell-time enhancing agents were intraperitoneally administered 30 minutes before, 3.5 hours after and 24 hours after the intravenous administration of PFOB.
$^a$S.D. refers to the Standard Deviation of the Mean
$^b$S.E. refers to the Standard Error to the Mean. S.E. = S.D.$\sqrt{N}$
$^c$N refers to the number of mice tested
$^d$p Value refers to "the probability of obtaining a result as extreme as or more extreme than the one observed if the dissimilarity is entirely due to chance alone." See, Medical Uses of Statistics (J.C. Bailor, III and F. Mostetler, eds. 1986). The usual significance level of 0.05 is used with a one-sided Student t-test comparing a saline control therapy with the results of the other categories of therapy under investigation (such as nicotinamide, isoniazid and neomycin).

RESULTS AND DISCUSSION

The results of this experiment demonstrate that of the three agents tested, only nicotinamide was capable of preventing weight loss. In fact, tumor bearing mice receiving nicotinamide gained weight over the course of the experiment. The beneficial effects of nicotinamide were also reflected in the behavior of the mice during the experiment. In particular, mice receiving nicotinamide had healthy coats and were alert. During the experiment, these mice actively resisted being handled. On the other hand, mice receiving other agents had scruffy coats and were lethargic. These mice did not resist being handled and were not interested in eating.

CONCLUSION

It has been demonstrated that the vascular dwell-time enhancing agent, nicotinamide, is capable of preventing weight loss and the onset of "flu-like" symptoms often triggered by the administration of a particulate therapeutic or particulate diagnostic agent. These symptoms are traditionally recognized as being the first signs of cachexia. Accordingly, the results of this experiment suggest that vascular dwell-time enhancing agents like nicotinamide are also capable of preventing and treating cachexia.

What is claimed is:

1. A method for preventing or treating a mammalian condition selected from the group consisting of hypoxemia and anemia, which method comprises the adjunct administration of a therapeutically effective amount of particulate blood substitute and an effective amount of a vascular dwell-time enhancing agent to said mammal in need of said prevention or treatment, wherein:
    i) said particulate blood stubstitute; (a) is delivered via the vascular compartment; and (b) comprises a fluorocarbon; and
    ii) said vascular dwell-time enhancing agent is selected from the group consisting of nicotinamide, nicotinic acid, AND, NADH and NADPH.

2. The method of claim 1 wherein said vascular dwell-time enhancing agent is nicotinamide.

3. The method of claim 1 wherein said vascular dwell-time enhancing agent is nicotinic acid.

4. The method of claim 1 wherein said particulate blood substitute is associated with a carrier.

5. The method of claim 4 wherein said carrier system comprises liposomes.

6. The method of claim 1 wherein said fluorocarbon is selected from the group consisting of a bis(F-alkyl)ethane, a cyclic fluorocarbon, a perfluorinated amine, a halogenated perfluorocarbon, a perfluoroalkylated ether, a perfluoroalkylated polyether, a perfluorocyclic ether, a perfluoroalkylated hydride and a fluorocarbon-hydrocarbon.

7. The method of claim 2 wherein said bis(F-alkyl)ethane is selected from the group consisting of $C_4F_9CH=CHC_4F_9$, i-$C_3F_7CH=CHC_6F_{13}$ and $C_6F_{13}CH=CHC_6F_{13}$, $C_3F_7CBr=CBrC_3F_7$, $C_3F_7CI=CIC_3F_7$, $C_2F_5CBr=CBrC_2F_5$ and $C_2F_5CI=CIChd 2F_5$.

8. The method of claim 2 wherein said cyclic fluorocarbon is selected from the group consisting of $C_{10}F_{18}$, F-adamantane, F-methyladamantane, F-1,3-dimethyladamantane, F-dimethylbicyclo[3,3,1]nonane and F-tri-methylbicyclo[3,3,1]nonane.

9. The method of claim 2 wherein said perfluorinated amine is selected from the group consisting of F-tripropylamine, F-tributylamine, F-4-methyloctylhydroquinolizine, F-n-methyl-decahydroisoquinoline, f-n-cyclohexylpyrrolidine and F-2-butyltetrahydrofuran.

10. The method of claim 2 wherein said perfluoroalkylated ether is selected from the group consisting of $(CF_3)_2CFO(CF_2CF_2)_3F$, $(C_6F_{13})_2O$ and $F[CF(CF)CFO]CHFCF$.

11. The method of claim 2 wherein said perfluoroalkylated polyether is selected from the group consisting of $(CF_3)_2CFO(CF_2CF_2)_2OCF(CF_3)_2$ and $(CF_3)_2CFO(CF_2CF_2)_3OCF(CF_3)$.

12. The method of claim 2 wherein said perfluoroalkylated hydride is selected from the group consisting of perfluorooctylhydride, perfluorononylhydride and perfluorodecylhydride.

13. The method of claim 2 wherein said fluorocarbon-hydrocarbon is selected from the group consisting of $C_8F_{17}C_2H_5$, $C_6F_{13}CH=CHC_6H_3$ and $C_8F_{17}R$, wherein R is any hydrocarbon with an organic functional group.

14. The method of claim 2 wherein said halogenated perfluorocarbon is selected from the group consisting of a monobrominated perfluorocarbon, a dibrominted perfluorocarbon, a monoiodinated perfluorocarbon and di-iodinated perfluorocarbon.

15. The method of claim 14 wherein said monobrominated perfluorocarbon is selected from the group consisting of 1-bromoheptadecafluorooctane, 1-bromopentadecafluoroheptane and 1-bromotridecafluorohexane.

16. The method of claim 14 wherein said dibrominated perfluorocarbon is selected from the group consisting of $C_6F_{12}Br_2$, $C_7F_{14}Br_2$ and $C_8F_{16}Br_2$.

17. A method for preventing or treating hypoxia associated with (a) a mammalian disorder selected from the group consisting of hemorrhagic shock and sepsis, or (b) a medical procedure selected from the group consisting of angioplasty and cardiopulmonary bypass surgery, which method comprises the adjunct administration of a therapeutically effective amount of a particulate blood substitute and an effective amount of a vascular dwell-time enhancing agent to a mammal in need of said prevention or treatment, wherein:

i) said particulate blood substitute; (a) is delivered via the vascular compartment; and (b) comprises a fluorocarbon; and ii) said vascular dwell-time enhancing agent is selected from the group consisting of nicotinamide, nicotinic acid, AND, NADH and NADPH.

18. The method of claim 17 wherein said vascular dwell-time enhancing agent is nicotinamide.

19. The method of claim 17 wherein said vascular dwell-time enhancing agent is nicotinic acid.

20. The method of claim 17 wherein said mammal is a human.

21. The method of claim 17 wherein said fluorocarbon is selected from the group consisting of a bis(F-alkyl)ethane, a cyclic fluorocarbon, a perfluorinated amine, a halogenated perfluorocarbon, a perfluoroalkylated ether, a perfluoroalkylated polyether, a perfluorocyclic ether, a perfluoroalkylated hydride and a fluorocarbon-hydrocarbon.

22. The method of claim 21 wherein said bis(F-alkyl)ethane is selected from the group consisting of $C_4F_9CH=CHC_4F_9$, i-$C_3F_7CLH=CHC_6F_{13}$ and $C_6F_{13}CH=CHC_6F_{13}$, $C_3F_7CBr=CBrC_3F_7$, $C_3F_7CI=CIC_3F_7$, $C_2F_5CBr=CBrC_2F_5$ and $C_2F_5CI=CIC_2F_5$.

23. The method of claim 21 wherein said cyclic fluorocarbon is selected from the group consisting of $C_{10}F_{18}$, F-adamantane, F-methyladamantane, F-1,3-dimethyladamantane, F-dimethylbicyclo[3,3,1]nonane and F-tri-methylbicyclo[3,3,1]nonane.

24. The method of claim 21 wherein said perfluorinated amine is selected from the group consisting of F-tripropylamine, F-tributylamine, F-4-methyloctylhydroquinolizine, F-n-methyl-decahydroisoquinoline, F-n-cyclohexylpyrrolidine and F-2-butyltetrahydrofuran.

25. The method of claim 21 wherein said perfluoroalkylated ether is selected from the group consisting of $(CF_3)_2CFO(CF_2CF_2)_3F$, $(C_6F_{13})_2O$ and $F[CF(CF)CFO]CHFCF$.

26. The method of claim 21 wherein said perfluoroalkylated polyether is selected from the group consisting of $(CF_3)_2CFO(CF_2CF_2)_2OCF(CF_3)_2$ and $(CF_3)_2CFO(CF_2CF_2)_3OCF(CF_3)$.

27. The method of claim 21 wherein said perfluoroalkylated hydride is selected from the group consisting of perfluoroocytylhydride, perfluorononylhydride and perfluorodecylhydride.

28. The method of claim 21 wherein said fluorocarbon-hydrocarbon is selected from the group consisting of $C_8F_{17}C_2H_5$, $C_6F_{13}CH=CHC_6H_{13}$ and $C_8F_{17}R$, wherein R is any hydrocarbon with an organic functional group.

29. The method of claim 21 wherein said halogenated perfluorocarbon is selected from the group consisting of a monobrominated perfluorocarbon, a dibrominated perfluorocarbon, a monoiodinated perfluorocarbon and di-iodinated perfluorocarbon.

30. The method of claim 29 wherein said monobrominated perfluorocarbon is selected from the group consisting of 1-bromoheptadecafluorooctane, 1-bromoentadeca-fluoroheptane and 1-bromotridecafluorohexane.

31. The method of claim 29 wherein said dibrominated perfluorocarbon is selected from the group consisting of $C_6F_{13}Br_2$, $C_7F_{14}Br_2$ and $C_8F_{16}Br_2$.

32. The method of claim 17 wherein said vascular dwell-time enhancing agent is associated with a carrier system.

33. The method of claim 32 wherein said carrier system comprises liposomes.

* * * * *